United States Patent [19]

Palmer

[11] 4,268,705

[45] May 19, 1981

[54] ADDITION OF MONOMER IN PRODUCTION OF LIQUID POLYMERS

[75] Inventor: Richard F. Palmer, Vancouver, Wash.

[73] Assignee: Phillips Petroleum Company, Bartlesville, Okla.

[21] Appl. No.: 132,559

[22] Filed: Mar. 21, 1980

[51] Int. Cl.³ .............................................. C07C 2/72
[52] U.S. Cl. ................................................... 585/429
[58] Field of Search ....................................... 585/429

[56] References Cited

U.S. PATENT DOCUMENTS

| | | | |
|---|---|---|---|
| 3,356,754 | 12/1967 | Wofford | 585/429 |
| 3,751,501 | 8/1973 | Kamienski et al. | |
| 4,041,088 | 8/1977 | Bach et al. | 585/429 |
| 4,049,732 | 9/1977 | Bach et al. | 585/429 |
| 4,060,492 | 11/1977 | Yasui et al. | |

*Primary Examiner*—Veronica O'Keefe

[57] ABSTRACT

Incremental addition of a monomer to be polymerized or copolymerized in a reaction medium comprising an alkyl aromatic, an organic lithium compound, and a transmetallation compound is effected to obtain liquid polymers and/or copolymers of narrow molecular weight range distribution suitable for conversion to lubricating oil as by hydrogenation. A conjugated diene, e.g., butadiene, alone, or together with a vinyl aromatic, e.g., styrene, is added incrementally to permit substantially complete reaction of at least the incrementally added monomer(s) and transmetallation to occur from living polymer to the alkyl aromatic in the reaction mass before addition of a succeeding increment.

10 Claims, No Drawings

ADDITION OF MONOMER IN PRODUCTION OF LIQUID POLYMERS

BRIEF SUMMARY OF THE INVENTION

Oligomerization and/or cooligomerization are effected under conditions permitting polymerization to proceed at a rate much faster than transmetallation rate, e.g., addition of a plurality of small monomer, e.g., diene and/or vinyl aromatic, increments, seriatim, with use of high organolithium compound/conjugated diene ratios, thus obtained, and relatively low temperatures with time between addition of increments to permit substantially complete conversion of the added monomer and complete transmetallation from a living polymer to alkyl aromatic present in the reaction mass. The products are useful in production of lubricants, e.g., lubricating oils, as by their hydrogenation.

DETAILED DESCRIPTION

This invention relates to the production of a liquid polymer. In one of its aspects the invention relates to the production of a liquid polydiene, e.g., polybutadiene. In another of its aspects it relates to production of a liquid copolymer of a conjugated diene and a vinyl aromatic. In a more specific aspect the invention relates to the production of liquid polybutadiene, oligomer, or a liquid cooligomer of, say, butadiene and styrene.

In one of its concepts the invention provides a process for the production of a liquid polydiene which comprises bringing into presence of an initiator for an oligomerization reaction, e.g., an organolithium compound, and a solvent, e.g., an alkyl-substituted aromatic hydrocarbon, successive increments of a conjugated diene, injecting the increments in a short time with good mixing or stirring and allowing time between addition of increments sufficient to permit substantially the complete conversion of the diene and complete transmetallation from the living oligomers formed to the alkyl aromatic. In another of its concepts, in a preferred sequence, the reactants are added to the reaction vessel in the following sequence: solvent, transmetallation compound(s), the first increment of conjugated diene, and finally the organolithium compound. In a further concept, next preferred, the sequence is: solvent, transmetallation compound(s), organolithium compound, and finally the first increment of the conjugated diene. In another of its concepts the invention provides, as described herein, a process for the production of liquid cooligomers as from a conjugated diene, e.g., butadiene and a vinyl aromatic, e.g., styrene, by adding separately or together increments of at least one, but preferably of both monomers, also as herein described.

In U.S. Pat. No. 3,356,754 issued Dec. 5, 1967, Clinton F. Wofford, there is disclosed the preparation of liquid polymers by the polymerization of conjugated dienes alone or in admixture with another conjugated diene or vinyl-substituted aromatic hydrocarbon in the presence of a catalyst formed on mixing an organolithium compound and an organic compound of an alkali metal selected from the group consisting of potassium, rubidium, and cesium together with at least 30 wt.% of a diluent employed being an alkyl-substituted aromatic hydrocarbon. The disclosure of the patent is incorporated herein by reference.

The present invention deals with polymerization of a conjugated diene and a conjugated diene with a vinyl aromatic by means of an initiator in the presence of a solvent that is involved in the chain transfer.

Suitable solvents are those disclosed in the patent. Included are the solvents:

| | |
|---|---|
| toluene | 1,4-di-n-propylbenzene |
| xylenes | 1,4-dimethyl-3-isopropylbenzene |
| 1,2,3-trimethylbenzene | 1-ethyl-2,5-di-n-propylbenzene |
| 1,2,4-trimethylbenzene | tert-butylbenzene |
| 1,3,5-trimethylbenzene | n-butylbenzene |
| 1,2,4,5-tetramethylbenzene | 1,3-di-n-butylbenzene |
| 1-methyl-2-ethylbenzene | n-amylbenzene |
| 2,4-diethylbenzene | 1-(n-amyl)-2-isopropylbenzene |
| ethylbenzene | 1,2-dimethyl-4-(n-hexyl)benzene |
| isopropylbenzene | n-octylbenzene |

The initiator for the oligomerization or cooligomerization reaction is an organolithium compound or a composition made by mixing (1) an organolithium compound and (2) transmetallation compounds comprising an organic compound of sodium, potassium, rubidium, or cesium and/or an aliphatic tertiary amine.

Examples of organolithium compounds are given in the patent and included are:

| | |
|---|---|
| methyllithium | 1,4-dilithiobutane |
| isopropyllithium | 1,10-dilithiodecane |
| n-butyllithium | 1,20-dilithioeicosane |
| sec-butyllithium | 1,4-dilithiocyclohexane |
| tert-octyllithium | 1,4-dilithio-2-butene |
| n-decyllithium | 1,8-dilithio-3-decene |
| phenyllithium | 1,4-dilithiobenzene |
| naphthyllithium | 1,2-dilithio-1,2-diphenylethane |
| 4-butylphenyllithium | 1,2-dilithio-1,8-diphenyloctane |
| p-tolyllithium | 1,3,5-trilithiopentane |
| 4-phenylbutyllithium | 1,5,15-trilithioeicosane |
| cyclohexyllithium | 1,3,5-trilithiocyclohexane |
| 4-butylcyclohexyllithium | 1,3,5,8-tetralithiodecane |
| 4-cyclohexylbutyllithium | 1,5,10,20-tetralithioeicosane |
| dilithiomethane | 1,2,4,6-tetralithiocyclohexane |
| | 4,4'-dilithiobiphenyl |
| and the like. | |

Examples of organic compounds of the alkali metals noted are also listed in the patent and included are all of those given in the patent in column 3, lines 13 to column 4, line 67. These compounds are not here repeated. These compounds do not form any part of the essence of the present invention but to the extent involved have been herein incorporated by reference.

Examples of tertiary amines are trimethylamine, triisopropylamine, and ditertiary amines such as N,N,N',N',-tetramethylethylenediamine (TMEDA) and 1-dimethylamino-2-ethoxyethane.

Conjugated dienes that can be used in the oligomerization reaction contain from 4 to 10 carbon atoms and include 1,3-butadiene, isoprene, 1,3-pentadiene, 2,3-dimethyl-1,3-butadiene, 2-methyl-1,3-pentadiene, 2,3-dimethyl-1,3-pentadiene, and 2-phenyl-1,3-butadiene.

Vinyl-substituted aromatics which can be used in the cooligomerization of the invention include styrene, and alpha-methylstyrene.

The liquid oligomers made according to the instant invention have molecular weights that lie substantially in the range that is suitable for conversion to lubricating oil, i.e., they contain from about 24 to about 44 carbon atoms and have a normal boiling point in the approximate range of from about 380° to 550° C.

The cooligomers of the invention, similarly, can be produced to have molecular weights in the range rendering them suitable for producing lubricating oils.

These, usually, will contain 23 to 43 carbon atoms and will boil in the approximate range of from about 390° to about 550° C.

Reaction Conditions

The polymerizations of this invention can be carried out at any temperature within the range of about −20° to 120° C.; but preferably the temperature will be in the range of from about 50° to about 90° C.

It is desirable for the reactants to be substantially in the liquid phase. Accordingly the reaction can be carried out at autogenous pressure. Neither the reaction rate nor the product of reaction appear to be changed significantly by raising the pressure above the vapor pressure of the monomeric conjugated diene at reaction temperature.

The process of this invention is carried out by the incremental addition of monomeric conjugated diene and/or vinyl aromatic to a reaction zone that contains solvent and initiator.

One skilled in the art in possession of this disclosure having studied the same, will be able to determine by routine test of the products obtained, the parameters or conditions of the reaction and of the amount or amounts of the increments to be added for optimum results, as well as whatever may be their order of addition when several monomers are used. To the extent that any monomer is added increment-wise and a time allowed for the extent of transmetallation desired to occur the basic concept of the invention is practiced. Thus, so long as a monomer addition is carefully controlled in increment size, time of addition, and the time at which it is added and during which it is added, there will result in inventive extent of control of the reaction, as desired.

Presently, as indicated in the data herein, the increment-wise addition is preferred now to be practiced as therein given.

The solvent as stated above is an alkyl-substituted aromatic hydrocarbon. It can be used undiluted or it can contain up to 50 weight percent of aliphatic and naphthenic hydrocarbons that are inert to the polymerization reaction. Examples of these diluents are isomeric butanes and pentanes, n-hexane, cyclohexane, methylcyclopentane, isooctane, and the like.

Polymerization can be started by combining reactants (but only a fraction of the conjugated diene) in any sequence. It is preferred, however, to add reactants to the reaction vessel in the following sequence: solvent, transmetallation compound(s), the first increment of conjugated diene (see below), finally the organolithium compound. Next preferred is the sequence solvent, transmetallation compounds, organolithium compound, finally the first increment of conjugated diene.

Because approximately one mole of the alkyl-substituted aromatic hydrocarbon solvent is incorporated chemically into each mole of liquid polymer produced, the quantity of said aromatic solvent to be taken cannot be less than the product of the number of moles of organolithium compound times the number of increments of monomer to be added; preferably a substantially larger quantity of the aromatic solvent will be used.

The quantity of organolithium compound to be used to make a run is not less than one gram equivalent per 1000 moles of conjugated diene, preferably one gram equivalent of organolithium compound per 400 moles of conjugated diene to be reacted is taken. As stated, the diene is added incrementally to the oligomerization zone. The quantity to be reacted is added in at least ten approximately equal portions; it can be divided into as many as 200 portions or even more.

Polymerization initiator is prepared by combination of organolithium compound with a transmetallation compound such as an organic compound of sodium, potassium, rubidium, or cesium and/or an aliphatic tertiary amine. Per equivalent of organolithium compound the moles of the two transmetallation compounds, respectively, to be taken can range from 0.01–3 and 0.01–6. The preferable concentration of the two transmetallation compounds, respectively, per equivalent of organolithium compound is 0.05–1 and 0.05–2.

With process conditions as herein defined the polymerizations of this invention are effected under conditions that permit the conjugated diene polymerization rate to proceed at a rate that is much faster than the transmetallation rate. This is favored by the use of high organolithium compound; conjugated diene ratios, i.e., the addition of small diene increments, and by the use of relatively low temperatures. Thus it is desirable to inject the diene increments in a very short time and to mix (stir) the mixture well. The time between the addition of increments should be long enough to permit essentially complete conversion of the monomeric diene, and any vinyl aromatic present, and complete transmetallation from the living oligomers to the alkyl aromatic. Generally this will be about 3 to 20 minutes, or longer.

The desired polymeric product of this invention can be recognized by a plot of its molecular weight distribution which will be symmetrical and narrow. Temperatures that are too high will produce polymers whose average molecular weight is too low; temperatures which are too low will produce oligomers or polymers whose average molecular weight is too high; the presence of an insufficient concentration of organolithium will produce a molecular weight distribution of increasing width.

EXAMPLE I

The following examples illustrate this invention. Table I summarizes the oligomerization recipes and reaction conditions for four runs. Runs 1 and 2 were made in a 300 mL autoclave, run 3 was made in a one-liter autoclave and run 4 was made in a one-gallon (3.8 liters) autoclave. Each run was made by adding to the dry, oxygen-free autoclave the toluene solvent, the transmetallation compound(s) dissolved in hexane, and incremental charge of butadiene, and finally the n-butyllithium dissolved in hexane. The run continued with the batch-wise addition of butadiene. In runs 1 and 2 it was added to the autoclave from stainless steel bombs pressurized with nitrogen gas. In runs 3 and 4 it was added with a positive displacement pump that was run intermittently during the polymerization. At the conclusion of each run the reactor was cooled in an ice bath, the contents were mixed with about one fourth to one half their volume of 2 N acetic acid to deactivate the initiator, washed with water, dried over a desiccant, and hydrogenated catalytically over palladium on carbon catalyst. Solvent was removed by distillation and the hydrogenated butadiene oligomer was distilled (under reduced pressure when necessary) through a Vigreux column to obtain the distillation analysis given in Table I. Run 1 is not considered to be a part of this invention; only five increments of butadiene were added.

TABLE I

| Run | Comparison 1 | Invention 2 | Invention 3 | Invention 4 |
|---|---|---|---|---|
| Reactants | | | | |
| Hexane, mL | 51 | 12 | 15 | 12 |
| Toluene, mL | 90 | 120 | 300 | 1295 |
| Butadiene (total), g | 55.8 | 72.7 | 160.6 | 730.6 |
| n-Butyllithium, mmoles | 25.2 | 11.6 | 10.5 | 34.0 |
| K tert-amyl oxide, mmoles | 0 | 0 | 0 | 8.5 |
| TMEDA, mmoles | 25.2 | 11.6 | 21.0 | 34.0 |
| Polymerization Conditions | | | | |
| Temperature, °C. | 120 | 113 | 93 | 60 |
| No. of increments | 5 | 14 | 45 | 80 |
| Time between increments, min. | 20 | 12.4 | 5.1 | 3.5 |
| Distillation Analysis of Hydrogenated Oligomer, Wt. % | | | | |
| Lights ($C_{11}$–$C_{22}$) | 18.7 | 18.2 | 8.3 | 10.3 |
| Lube Oil ($C_{23}$–$C_{43}$) | 69.9 | 72.7 | 89.7 | 83.1 |
| Heavies ($>C_{43}$) | 11.5 | 9.1 | 2.0 | 6.6 |
| Properties of Lube Oil Fraction | | | | |
| Boiling range, °C. | 370–529 | 392–535 | 380–530 | 380–545 |
| Phenyl groups/molecule (NMR) | — | — | — | 0.57 |
| Methyl groups/butadiene conv. (NMR) | — | — | — | 0.79 |
| Viscosity at 100° F., SUS | 375 | 153.7 | 184 | 269 |
| Viscosity at 210° F., SUS | 53.9 | 43.1 | 45.3 | 51.8 |
| Viscosity index | 81 | 93 | 96 | 99 |
| Pour Point, °C. | −25 | −30 | −40 | −34 |

EXAMPLE II

Preparation of liquid polymer by cooligomerization of butadiene and styrene is illustrated in this example. Through a port in a dry, nitrogen-purged 1-liter autoclave 240 mL of toluene, 5.27 mL of a 2.54 molar solution of TMEDA in toluene and 13.7 mL of a 0.244 molar solution of potassium tert-amyl oxide in toluene were placed. The autoclave was evacuated three times, with the vacuum being released each time with dry nitrogen to insure removal of all oxygen. A 2.89 mL increment of a 50:50 (weight) mixture of butadiene-styrene was added, then 8.65 mL of 1.55 molar n-butyllithium in hexane. Forty-five additional increments of butadiene-styrene of the same size were added by pump that operated for 15 seconds, then was off for 3 minutes. Temperature of the reaction mixture during the addition ranged from 57°–71° C. At the conclusion of the oligomerization reaction the autoclave was cooled to about 25° C. and catalyst was deactivated by the addition of 50 mL of 2 N aqueous acetic acid. The product was washed with water and dried over anhydrous MgSO$_4$. Toluene solvent was removed on a rotary evaporator and the oligomer, diluted with 50 mL of hexane, was placed in an autoclave together with 0.5 g of 5% Pt on carbon hydrogenation catalyst. It was hydrogenated for about 3 hours at 160° C., with stirring, under 425–475 psig hydrogen pressure. Hydrogenated oil was rinsed from the autoclave with hexane which was then removed on a rotary evaporator. The oil was distilled through a Vigreux column at reduced pressure and the fraction boiling between 383°–525° C. (corrected) was tested. This fraction comprised 91.5 wt.% of the liquid polymer. It had the following properties:
Viscosity at 40° C., SUS: 120.3
Viscosity at 100° C., SUS: 40.8
Viscosity index: 75
Pour point, °C.: −45

Accordingly, it is an object of the present invention to provide an oligomer or cooligomer-containing product having a relatively narrow molecular weight distribution which is symmetrical and narrow. In another object of the invention to control an oligomerization or cooligomerization reaction to form a polymeric product having a high yield in the lubricating oil molecular weight range.

Other aspects, concepts, objects, and the several advantages of the invention are apparent from a study of this disclosure and the appended claims.

According to the present invention, polymerization of a conjugated diene or such a diene and a vinyl aromatic is effected in a reaction medium to which at least the conjugated diene is added in a number of increments which are relatively small; the increments are added in a short time under good mixing conditions and the time between addition of the increments is sufficiently long to permit substantially the complete conversion of at least the diene and essentially or substantially the complete transmetallation from living polymer to the alkyl aromatic which is present.

In a now preferred form of the invention, the quantity of diene or monomer ultimately to have been added is divided into at least 10 portions, preferably approximately equal portions, each portion forming an increment to be added according to the invention. More preferably, according to the invention, the diene or monomers to be reacted are divided into as many as 200 portions or even more to permit, ultimately, the obtaining of the desired product, herein described. The addition time for each increment can be varied. Initial increments may be added over a shorter time than later-added increments. Depending upon reaction conditions and the condition of the reaction mass, the time allowed or to be allowed for the transmetallation can also be varied. One skilled in the polymerization art, having studied this disclosure can determine the optimum conditions, increment sizes and their rates and times of addition by performing simple, routine tests.

In U.S. Pat. No. 3,751,501 issued Aug. 7, 1973, it is described, in column 5 in lines 15 et seq, that the conjugated diene monomer is to be added in a gradual and controlled manner. The present invention is to be distinguished sharply from such addition. The gradual and controlled manner addition described in column 5 in the paragraph beginning in line 16 of the patent is also herein noted and is to be distinguished from the manner of addition, increment-wise, of the present invention.

The present invention critically provides the time for transmetallation to occur. This cannot be the case with continuous or even continual addition unless prescribed as in the present disclosure.

Reasonable variation and modification are possible within the scope of the foregoing disclosure and the appended claims to the invention the essence of which is that in the polymerization of at least one monomer, say, a conjugated diene and/or a vinyl aromatic, the monomer is added increment-wise, each increment being relatively small and the time between addition of each monomer added increment-wise being sufficient to allow for substantially complete conversion of the added monomer and substantially complete transmetallation from living polymer formed to the alkyl aromatic which is present.

I claim:

1. The polymerization of at least one of a conjugated diene and a vinyl aromatic in the presence of a reaction medium containing an alkyl aromatic, an organolithium compound and a transmetallation compound and adapted to produce a liquid polymer, which comprises adding at least one monomer in increments and allowing time between addition of increments for substantially complete conversion of the incrementally added monomer and substantially complete transmetallation from living polymer formed to alkyl aromatic present in the medium.

2. A process according to claim 1 wherein the diene is butadiene.

3. A process according to claim 1 wherein vinyl aromatic is at least one of styrene and alphamethyl styrene, alkyl aromatic is toluene and there are present also n-butyllithium and tetramethylethylenediamine.

4. A process according to claim 1 wherein at least ten increments of approximately equal portions are added.

5. A process according to claim 1 wherein there is present potassium tert-amyl oxide.

6. A process according to claim 1 wherein the temperature during the process is within the approximate range of from about $-20°$ to about $120°$ C.

7. A process according to claim 1 wherein the temperature during the process is in the approximate range of from about $50°$ to about $90°$ C.

8. A process according to claim 1 wherein the conjugated diene contains from 4 to 10 carbon atoms.

9. A process according to claim 8 wherein the conjugated diene is at least one selected from 1,3-butadiene, isoprene, 1,3-pentadiene, 2,3-dimethyl-1,3-butadiene, 2-methyl-1,3-pentadiene, 2,3-dimethyl-1,3-pentadiene, and 2-phenyl-1,3-butadiene.

10. A process according to claim 1 wherein an initiator employed for the oligomerization reaction is at least one of an organolithium compound and a composition made by mixing an organolithium compound and a transmetallation compound comprising an organic compound of an alkali metal and/or an aliphatic tertiary amine.

* * * * *